United States Patent [19]

Child et al.

[11] Patent Number: 5,414,186
[45] Date of Patent: May 9, 1995

[54] LIQUID ACID ALKYLATION CATALYST AND ISOPARAFFIN-OLEFIN ALKYLATION PROCESS

[75] Inventors: Jonathan E. Child; Tomas R. Melli, both of Sewell, N.J.

[73] Assignee: Mobil Oil Corporation, Fairfax, Va.

[21] Appl. No.: 136,481

[22] Filed: Oct. 13, 1993

Related U.S. Application Data

[63] Continuation of Ser. No. 925,009, Aug. 5, 1992, abandoned.

[51] Int. Cl.$^6$ .............................. C07C 2/62; C07C 7/10
[52] U.S. Cl. ..................................... 585/724; 585/802
[58] Field of Search ................................ 585/724, 802

[56] References Cited

U.S. PATENT DOCUMENTS

| | | | |
|---|---|---|---|
| 2,615,908 | 10/1952 | McCaulay et al. | 260/438 |
| 3,531,546 | 9/1970 | Hervert | 260/683.51 |
| 3,778,489 | 12/1973 | Parker et al. | 260/683.43 |
| 3,795,712 | 3/1974 | Torck et al. | 585/724 |
| 3,856,764 | 12/1974 | Throckmorton et al. | 260/82.1 |
| 3,887,635 | 6/1975 | Parker et al. | 585/724 |
| 4,025,577 | 5/1977 | Siskin et al. | 260/683.51 |
| 4,058,575 | 11/1977 | Cahn et al. | 585/724 |
| 4,099,924 | 7/1978 | Berkman et al. | 23/273 |
| 4,225,742 | 9/1980 | Hutson, Jr. | 585/723 |
| 4,236,036 | 11/1980 | Dixon et al. | 585/724 |
| 4,316,998 | 2/1982 | Van Pool | 585/723 |
| 4,467,131 | 8/1984 | Washer et al. | 585/723 |
| 4,777,323 | 10/1988 | Hann et al. | 585/723 |
| 4,938,935 | 7/1990 | Audeh et al. | 423/240 |
| 4,938,936 | 7/1990 | Yan | 423/240 |
| 4,985,220 | 1/1991 | Audeh et al. | 423/240 |
| 5,073,674 | 12/1991 | Olah | 585/725 |
| 5,264,647 | 11/1993 | Castman et al. | 585/724 |

OTHER PUBLICATIONS

L. F. Albright et al., "Alkylation of Isobutane with C$_4$ Olefins", 27 *Ind. Eng. Chem. Res.*, 381–397 (1988).
1 *Handbook of Petroleum Refining Processes*, 23–28 (R. A. Meyers, ed., 1986).

*Primary Examiner*—Asok Pal
*Attorney, Agent, or Firm*—Alexander J. McKillop; Dennis P. Santini; Robert B. Furr, Jr.

[57] ABSTRACT

The present invention provides an acid catalyzed isoparaffin-olefin alkylation process which improves process stability and safety by storing the acid in an excess of an additive which reduces the fuming tendency of the mixture, for example, a sulfone. Acid is stripped from the additive and concentrated prior to charging the acid to the alkylation reaction zone. Specifically, because the stored solution of acid in the additive is more dilute than can be effectively used for isoparaffin-olefin alkylation, the acid is concentrated prior to charging the catalyst mixture to the reaction zone. The invention solves the problem of conjunct polymer accumulation by diluting the conjunct polymer with a relatively large volume of the additive and continuously regenerating a slipstream of the dilute acid/additive mixture.

19 Claims, 1 Drawing Sheet

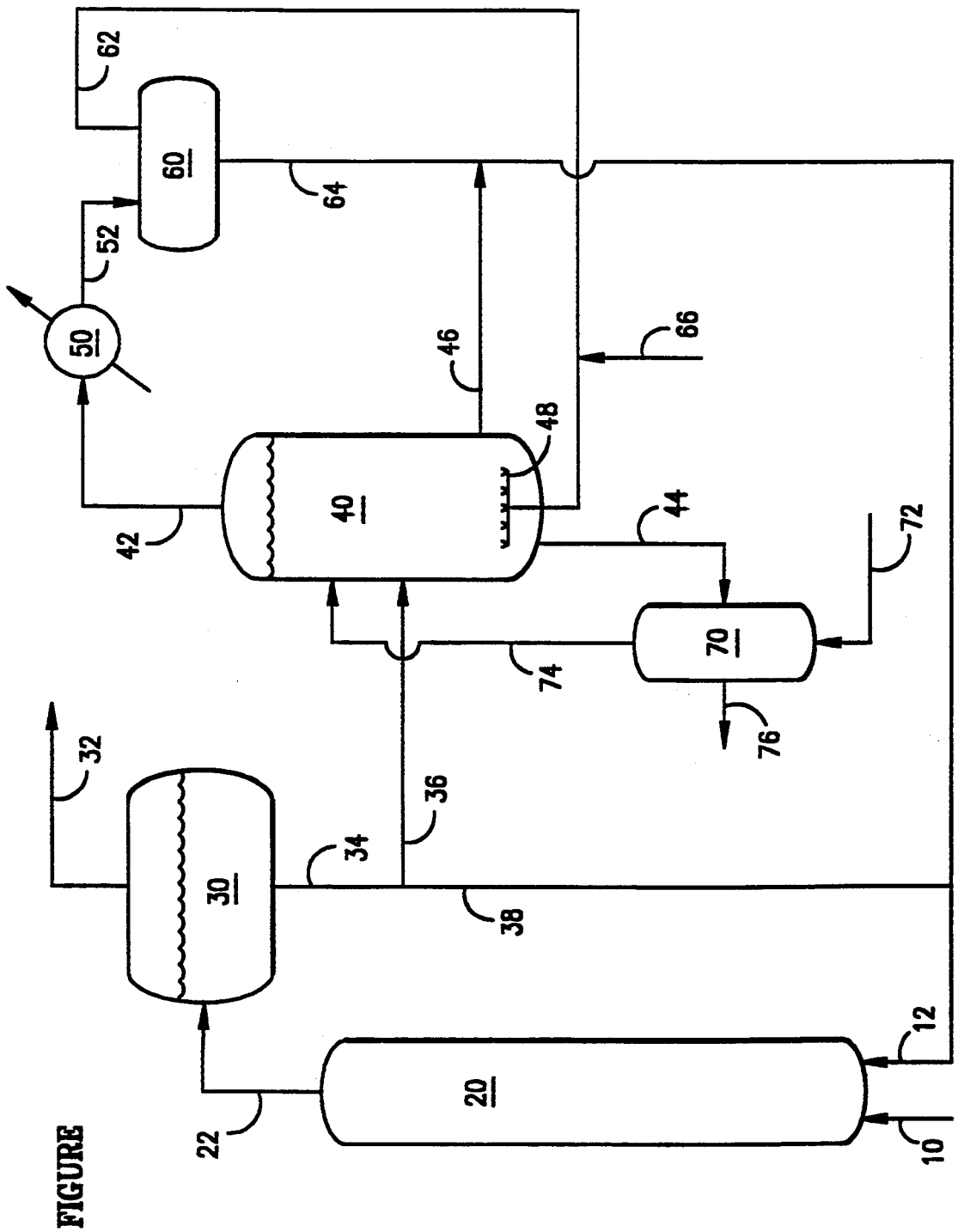
FIGURE

LIQUID ACID ALKYLATION CATALYST AND ISOPARAFFIN-OLEFIN ALKYLATION PROCESS

This is a continuation of application Ser. No. 07/925,009, filed on Aug. 5, 1992, now abandoned.

FIELD OF THE INVENTION

The present invention relates to the art of catalytic alkylation. More specifically, the invention relates to a liquid alkylation catalyst and an isoparaffin-olefin alkylation process. Particularly, the invention provides a liquid alkylation catalyst composition which avoids many of the safety and environmental concerns associated with concentrated hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its low aromatic and sulfur content.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry uses anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape, possibly creating a vapor cloud that could be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

But it would be particularly desirable to provide an additive which decreases the cloud forming tendency of HF without compromising its activity as an isoparaffin-olefin alkylation catalyst. Solvents and complexing agents for hydrofluoric acid have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10–24.

U.S. Pat. No. 3,531,546 to Hervert discloses a HF—$CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula $R—SO_2—R'$, where $R$ and $R'$ are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. Nos. 4,025,577 and 4,099,924 to Siskin et al. report the use of alkylation catalyst compositions containing HF, a metal halide, and sulfolane.

U.S. Pat. No. 5,073,674 to Olah relates to hydrofluoric acid-containing alkylation catalysts which are said to exhibit decreased fuming tendency in comparison with heat HF.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

Certain additives have recently been found to mitigate the cloud forming tendency of strong Bronsted acids useful in isoparaffin-olefin alkylation while preserving most of the acid's activity as an alkylation catalyst. Diluting the acid with such additives, while effective in improving safety, affects changes in process chemistry which complicate process control. Specifically, it has been found that diluting the acid with certain additives increases the sensitivity of the acid to conjunct polymer formation. The accumulation of these conjunct polymeric byproducts is believed to interfere with isoparaffin-olefin alkylation catalysis.

SUMMARY OF THE INVENTION

The present invention provides an acid catalyzed isoparaffin-olefin alkylation process which improves process stability and safety by storing the acid in an excess of an additive which reduces the fuming tendency of the mixture, for example, a sulfone. Acid is stripped from the additive and concentrated prior to charging the acid to the alkylation reaction zone. Specifically, because the stored solution of acid in the additive is more dilute than can be effectively used for isoparaffin-olefin alkylation, the acid is concentrated prior to charging the catalyst mixture to the reaction zone. The invention solves the problem of conjunct polymer accumulation by diluting the conjunct polymer with a relatively large volume of the additive and continuously regenerating a slipstream of the dilute acid/additive mixture.

The present invention provides a process for alkylating an isoparaffin with an olefin comprising the steps of:
  (a) providing a reaction zone for contacting at least one isoparaffin with at least one olefin in the presence of an alkylation catalyst;
  (b) charging said alkylation catalyst to said reaction zone, said alkylation catalyst comprising at least one acid selected from the group consisting of hydrofluoric acid and the halogen-substituted sulfonic acids, together with a vapor pressure reducing additive, wherein the concentration of said vapor pressure reducing additive in said acid is from about 10 to about 80 mole percent;
  (c) withdrawing an effluent stream containing alkylation catalyst and hydrocarbon product from said reaction zone;
  (d) separating said withdrawn effluent stream of step
  (c) into an alkylate-enriched hydrocarbon product stream and an alkylation catalyst-enriched stream;
  (e) recycling a first portion of said alkylation catalyst-enriched stream to said reaction zone of step (b);
  (f) flowing a second portion of said alkylation catalyst-enriched stream to an acid storage zone wherein the concentration of said vapor pressure reducing additive within said acid storage zone exceeds the concentration of said vapor pressure reducing additive in said second portion of said alkylation catalyst-enriched stream;
  (g) charging a stripping fluid to said acid storage zone;
  (h) withdrawing acid-enriched stripping fluid from said acid storage zone;
  (i) withdrawing a mixture of said acid and vapor pressure reducing additive from said acid storage zone;
  (j) mixing said stripped acid of step (h) with said withdrawn stream of step (i); and
  (k) flowing said mixed stream of step (j) to said alkylation reaction zone.

The acid-enriched stripping fluid may be mixed with the withdrawn stream of acid and vapor pressure reducing additive and charged to the alkylation reaction zone, or the stripping fluid may be separated from the acid and recycled.

BRIEF DESCRIPTION OF THE DRAWING

The Figure is a simplified schematic diagram illustrating major processing steps of an embodiment of the present invention.

DETAILED DESCRIPTION

The invention provides an isoparaffin-olefin alkylation catalyst which provides commercially useful alkylation activity while overcoming disadvantages associated with concentrated HF and metal halides. Specifically, this invention stores the bulk of its strong liquid acid inventory in a form which cannot evaporate under ambient conditions in significant quantities to form vapor clouds.
Feedstocks Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, isopentene, 1-pentene, 2-pentene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 20:1.

Catalyst Composition

The catalyst composition which is charged to the alkylation reaction zone of the present invention comprises from about 10 to about 90 weight percent acid and from about 10 to about 90 weight percent of an additive, for example, a sulfone having the formula R—$SO_2$—R' as described in commonly-assigned U.S. application Ser. No. 07/719,879, filed Jun. 6, 1991, now abandoned (Mobil Docket 6251). Sulfolane is a particularly preferred sulfone component of the alkylation catalyst composition of the present invention. Other additives which are useful in the present invention include nitroalkanes as taught in commonly-assigned U.S. application Ser. No. 07/719,277, filed Jun. 21, 1991, now U.S. Pat. No. 5,196,628 (Mobil Docket 6185), organic carbonates as taught in U.S. application Ser. No. 07/719,276, filed Jun. 21, 1991, now U.S. Pat. No. 5,220,096 (Mobil Docket 6186), perfluoro compounds as taught in U.S. application Ser. No. 07/719,275 filed Jun. 21, 1991, (Mobil Docket 6222), perhalogenated alkanes as taught in U.S. application Ser. No. 07/720,124, filed Jun. 21, 1991, now abandoned (Mobil Docket 6238), halogenated sulfonic acids as taught in U.S. application Ser. No. 07/719,278, filed Jun. 6, 1991, now abandoned (Mobil Docket 6249), halogenated alcohols as taught in U.S. application Ser. No. 07/720,125, filed Jun. 21, 1991, now abandoned (Mobil Docket 6250), and carboxylic acids as taught in U.S. application Ser. No. 07/761,567, filed Sep. 18, 1991, now U.S. Pat. No. 5,202,518 (Mobil Docket 6366), merely to name a few. The disclosures of these commonly assigned applications are incorporated by reference as if set forth at length herein. The alkylation catalyst composition preferably comprises from about 10 to about 80 weight percent of the vapor pressure reducing additive, more preferably from about 20 to about 60 weight percent of the vapor pressure reducing additive, with the substantial balance of the acid/sulfone catalyst composition comprising at least one selected from the group consisting of hydrofluoric acid and the halogenated sulfonic acids.

Within the acid storage zone, the acid concentration generally ranges from about 2 to about 50 weight percent acid, typically from about 10 to about 40 weight percent, and more more typically from about 20 to about 30 weight percent. The preferred extent of dilution in the storage zone is a function of the selected acid/additive combination, and the dilution is preferably sufficient to reduce the vapor pressure of the mixture to less than atmospheric pressure at the greater of ambient or storage temperature.

Process Conditions

The catalyst composition of the present invention may be readily substituted for the concentrated hydrofluoric acid catalyst in an existing hydrofluoric acid alkylation process unit, for example, a riser reactor alkylation process unit, or a pump-around heat exchange unit, without substantial equipment modifications. Accordingly, the conversion conditions for the process of the present invention resemble those of typical commercial hydrofluoric acid alkylation processes.

The present alkylation process is suitably conducted at temperatures of from about 10° to about 500° C., preferably from about 10° to about 200° C., and more preferably from about 20° C. to about 60° C. Pressure is maintained to ensure a liquid phase in the alkylation reaction zone. Pressures typically range from from about 20 to about 1200 psig, preferably from about 50 to about 500 psig. Olefin feed rates generally range from about 0.01 to about 10 WHSV and more preferably from about 0.05 to about 5 hr$^{-1}$ WHSV. The mixed isoparaffin-olefin reactants may be contacted with the catalyst composition of the invention in any suitable reaction vessel, examples of which include stirred-tank reactors, pump-around reactors, as well as riser-type reactors. Contact time for the mixed isoparaffin-olefin feed and the catalyst composition of the invention typically are within the range of from about 0.1 second to about 100 minutes, and more preferably from about 10 seconds to about 2 minutes.

The vapor pressure reducing additive component of the alkylation catalyst composition may be added by injection directly into the alkylation process unit, or may be mixed with the hydrocarbon charge, or may be mixed with the fresh and/or the circulating acid catalyst component, or with a stream of mixed acid/additive catalyst. Downstream from the alkylation reaction zone, the additive is preferably separated from the alkylate product stream, mixed with fresh and/or circulating acid and/or circulating acid/additive catalyst mixture, and recycled to the alkylation reaction zone. The particular separation technique selected, however, depends upon the characteristics of the selected additive.

The additive may partition between the acid and the alkylate-containing hydrocarbon reactor effluent, or may remain in either the hydrocarbon or the acid phase, or may form a third discrete phase, depending upon the characteristics of the selected additive. If the boiling point of the selected additive does not overlap major hydrocarbon products, distillation is preferred to separate and recycle the additive. Higher boiling (e.g. >200° C.) additives may require extraction (for example, liquid-liquid solvent extraction) to be efficiently recovered from alkylation byproducts such as ASO (acid soluble oil).

Acid Stripping

The process of this invention stores the acid component of the alkylation catalyst in a markedly more dilute form than would be useful as an isoparaffin-olefin alkylation catalyst. The acid is transferred from the storage facility to the alkylation reaction zone by stripping the acid from the acid/additive solution using a stripping fluid. The acid is then mixed with a stream of additive-enriched liquid withdrawn from the acid storage facility to adjust the acid concentration in the catalyst mixture before charging the mixture to the alkylation reaction zone. The stripping fluid may be inert to the downstream alkylation reaction, in which case it may optionally be carried with the stripped acid into the alkylation reaction zone. Nitrogen is one example of a useful inert stripping fluids. Alternatively, the acid may be stripped from the acid/additive mixture with a feed isoparaffin for the downstream alkylation reaction. Isobutane, a particularly preferred feed isoparaffin, is an example of a useful stripping fluid which is preferably charged to the alkylation reaction zone with the stripped acid.

Embodiment

Referring now to the Figure, a mixture of olefin and isoparaffin is charged through line 10 to a lower portion of riser reactor 20. Catalyst enters riser reactor 20 through line 12 at a rate sufficient to provide a ratio of acid to total hydrocarbon feed in the range of from about 1:1 to about 10:1. The mixture of catalyst and hydrocarbon reacts exothermically as it flows upwardly through the reactor. For this reason, the reactor may optionally contain means for removing sensible heat from the reactor, for example, heat exchange tubing such as cooling coils to circulate a chilled fluid in indirect contact with the mixture of catalyst and reactants.

The mixture of catalyst and reactants, now enriched in alkylate product, flows from the top of riser reactor 20 through line 22 to settler 30. The alkylate-enriched hydrocarbon product is withdrawn from an upper section of settler 30 via line 32. The catalyst is withdrawn from settler 30 through line 34, and is split between lines 36 and 38. Flow through line 36 may comprise from about 1 to about 90 percent of the total flow through line 34 and typically comprises from about 5 to about 40 percent of the total flow through line 34.

The slipstream of mixed acid and sulfolane flows through line 36 to acid storage zone 40 where the acid is diluted as it flows into the storage zone. The volume of the acid storage zone is preferably as large as economically feasible, and must be sufficient to dilute the acid to a concentration of less than about 50 weight percent.

The acid is withdrawn from the acid storage zone by stripping the acid from the sulfolane. A stripping fluid enters a lower section of acid storage zone 40 via line 62 and flows into the mixture of acid and sulfolane through distributor 48. The acid-enriched stripping fluid then flows from an upper portion of acid storage zone 40 via line 42 to overhead condenser 50, where the mixture of acid and stripping fluid is partially condensed. The partially condensed mixture is transferred via line 52 to knockout drum 60 which separates the condensed acid (withdrawn through line 64) from the stripping fluid (withdrawn through line 62). The condensed acid mixes with a stream enriched in sulfolane withdrawn from the acid storage zone 40 through line 46. The total quantities of acid and sulfolane charged to the reactor 20 through lines 64 and 46 are approximately equal to those in line 36 to maintain relatively constant concentrations of acid and sulfolane in the reactor 20.

The mixed stream of acid and sulfolane continues through line 64 and mixes with recycled acid catalyst from line 38. The total acid catalyst charge to the reaction zone 20 then flows to a lower section of reaction zone 20 via line 12.

Line 44 continuously draws a slipstream containing sulfolane and acid from a lower section of acid storage zone 40 and charges the mixture to stripper 70 where a second stripping fluid such as isobutane strips acid and sulfolane from the polymerized side products of the alkylation reaction, which are commonly referred to in the industry as acid soluble oil, or ASO. Alternatively, the slipstream may be charged to other suitable regeneration facilities and then recycled to the acid storage zone 40.

Changes and modifications in the specifically described embodiments can be carried out without departing from the scope of the invention which is intended to be limited only by the scope of the appended claims.

We claim:

1. A process for alkylating an isoparaffin with an olefin comprising the steps of:
   (a) providing an alkylation reaction zone for contacting at least one isoparaffin with at least one olefin in the presence of an alkylation catalyst;
   (b) charging said isoparaffin, said olefin, and said alkylation catalyst to said alkylation reaction zone, said alkylation catalyst comprising at least one acid selected from the group consisting of hydrofluoric acid and the halogen-substituted sulfonic acids, together with a vapor pressure reducing additive, wherein the concentration of vapor pressure reducing additive in said acid is from about 10 to about 80 weight percent;
   (c) withdrawing an effluent stream containing alkylation catalyst, hydrocarbon product, and conjunct polymer products of said alkylation reaction from said reaction zone;
   (d) separating said withdrawn effluent stream of step (c) into an alkylate-enriched hydrocarbon product stream and an alkylation catalyst-enriched stream;
   (e) recycling a first portion of said alkylation catalyst-enriched stream to said reaction zone of step (b);
   (f) flowing a second portion of said alkylation catalyst-enriched stream to an acid storage zone wherein the concentration of said vapor pressure reducing additive within said acid storage zone exceeds the concentration of said vapor pressure reducing additive in said second portion of said alkylation catalyst-enriched stream and wherein the concentration of said acid is from about 20 to about 50 weight percent;
   (g) charging a first stripping fluid to said acid storage zone;
   (h) withdrawing acid-enriched first stripping fluid from said acid storage zone and separating condensed acid from said first stripping fluid;
   (i) withdrawing a first stream of said acid and said vapor pressure reducing additive from said acid storage zone;
   (j) mixing said condensed acid of step (h) with said withdrawn first stream of step (i);
   (k) flowing said mixed stream of step (j) to said alkylation reaction zone;
   (l) withdrawing a second stream containing said acid, said vapor pressure reducing additive and said polymerized side products of said alkylation reaction from said acid storage zone and flowing said second stream to a catalyst stripper;
   (m) charging a second stripping fluid to said catalyst stripper to strip said acid and said vapor pressure reducing additive from said conjunct polymer products of said alkylation reaction to produce an overhead stream enriched in said acid and said vapor pressure reducing additive;
   (n) recycling said overhead stream of step (m) to said acid storage zone.

2. The process of claim 1 wherein said separation step (d) comprises gravitational separation.

3. The process of claim 2 wherein said gravitational separation step comprises decantation.

4. The process of claim 1 further comprising controlling the ratio of acid to hydrocarbon within said reaction zone by controlling the flow of stripping fluid to said acid storage zone.

5. The process of claim 1 wherein said stripping fluid comprises an isoparaffin.

6. The process of claim 5 wherein said isoparaffin is isobutane.

7. The process of claim 1 wherein said stripping fluid is essentially inert to said isoparaffin and said olefin.

8. The process of claim 7 wherein said essentially inert stripping fluid is nitrogen.

9. The process of claim 1 wherein said vapor pressure reducing additive is selected from the group consisting of sulfones, nitroalkanes, organic carbonates, perhalogenated alkanes, halogenated sulfonic acids, halogenated alcohols, and carboxylic acids.

10. The process of claim 1 wherein said vapor pressure reducing additive is sulfolane.

11. The process of claim 1 wherein the dilution of said acid with said vapor pressure reducing additive is sufficient to reduce the vapor pressure of the mixture of acid and vapor pressure reducing additive to less than atmospheric pressure at the greater of ambient or acid storage zone temperature.

12. A process for alkylating an isoparaffin with an olefin comprising the steps of:
   (a) providing an alkylation reaction zone for contacting at least one isoparaffin with at least one olefin in the presence of an alkylation catalyst;
   (b) charging said isoparaffin, said olefin, and said alkylation catalyst to said alkylation reaction zone, said alkylation catalyst comprising at least one acid selected from the group consisting of hydrofluoric acid and the halogen-substituted sulfonic acid, together with a vapor pressure-reducing additive, selected from the group consisting of sulfones, nitroalkanes, organic carbonates, perhalogenated alkanes, halogenated alcohols, and carboxylic acids, wherein said acid is diluted with said vapor pressure-reducing additive to an extent sufficient to reduce the vapor pressure of the mixture to less than atmospheric pressure at the greater of ambient or acid storage zone temperature;
   (c) withdrawing an effluent stream containing alkylation catalyst, hydrocarbon product, and conjunct polymer products of said alkylation reaction from said reaction zone;
   (d) separating said withdrawn effluent stream of step (c) into an alkylate-enriched hydrocarbon product stream and an alkylation catalyst-enriched stream;
   (e) recycling a first portion of said alkylation catalyst-enriched stream to said reaction zone of step (b);
   (f) flowing a second portion of said alkylation catalyst-enriched stream to an acid storage zone wherein the concentration of said vapor pressure reducing additive within said acid storage zone exceeds the concentration of said vapor pressure reducing additive in said second portion of said alkylation catalyst-enriched stream and wherein the concentration of said acid is from about 20 to about 50 weight percent;

(g) charging a stripping fluid to said acid storage zone;

(h) withdrawing acid-enriched stripping fluid from said acid storage zone and separating condensed acid from said stripping fluid;

(i) withdrawing a mixture of said acid and said vapor pressure reducing additive from said acid storage zone;

(j) mixing said condensed acid of step (h) with said withdrawn first stream of step (i); and (k) flowing said mixed stream of step (j) to said alkylation reaction zone;

(l) withdrawing a second stream containing said acid, said vapor pressure reducing additive and said polymerized side products of said alkylation reaction from said acid storage zone and flowing said second stream to a catalyst stripper;

(m) charging a second stripping fluid to said catalyst stripper to strip said acid and said vapor pressure reducing additive from said conjunct polymer products of said alkylation reaction to produce an overhead stream enriched in said acid and said vapor pressure reducing additive; and (n) recycling said overhead stream of step (m) to said acid storage zone.

13. The process of claim 12 wherein said separation step (d) comprises gravitational separation.

14. The process of claim 13 wherein said gravitational separation step comprises decantation.

15. The process of claim 12 further comprising controlling the ratio of acid to hydrocarbon within said reaction zone by controlling the flow of said first stripping fluid to said acid storage zone.

16. The process of claim 12 wherein said stripping fluids comprise an isoparaffin.

17. The process of claim 16 wherein said isoparaffin is isobutane.

18. The process of claim 12 wherein said stripping fluids are essentially inert to said isoparaffin and said olefin.

19. The process of claim 18 wherein said stripping fluids are nitrogen.

* * * * *